(12) United States Patent  
Smith

(10) Patent No.: US 7,568,967 B2  
(45) Date of Patent: Aug. 4, 2009

(54) BREAST SLING

(76) Inventor: Veronica C. Smith, 999 Marina Dr. South, Richmond, CA (US) 94804

( * ) Notice: Subject to any disclaimer, the term of this patent is extended or adjusted under 35 U.S.C. 154(b) by 152 days.

(21) Appl. No.: 11/229,977

(22) Filed: Sep. 19, 2005

(65) Prior Publication Data

US 2006/0211334 A1     Sep. 21, 2006

Related U.S. Application Data

(60) Provisional application No. 60/622,387, filed on Oct. 27, 2004.

(51) Int. Cl.
*A41D 3/00* (2006.01)
(52) U.S. Cl. .............................. 450/1; 450/62; 128/874
(58) Field of Classification Search ............... 450/1–3, 450/5, 7–10, 12–14, 17, 18, 22, 25, 26, 59, 450/62, 63, 85, 54–58, 39; 128/869, 870, 128/873, 874, 90.1, 99.1, 100.1, 101.1; 602/41, 602/60, 61; 2/73, 78.1–78.4, 104, 106, 69, 2/310–312, 338, 315, 317, 318, 319, 308, 2/331, 335, 336, 321, 171, 171.8
See application file for complete search history.

(56) References Cited

U.S. PATENT DOCUMENTS

| | | | | |
|---|---|---|---|---|
| 5,081,714 A | * | 1/1992 | Liu | 2/418 |
| 5,116,306 A | * | 5/1992 | Zander | 602/19 |
| 5,147,261 A | * | 9/1992 | Smith et al. | 482/106 |
| 5,539,933 A | * | 7/1996 | Garber et al. | 2/311 |
| 6,755,717 B2 | * | 6/2004 | Smith | 450/1 |

* cited by examiner

*Primary Examiner*—Gloria Hale
(74) *Attorney, Agent, or Firm*—David E Newhouse, Esq

(57) ABSTRACT

A breast sling for positioning and stabilizing a woman's breasts following cosmetic or reconstructive breast surgery includes a wide, plush pile, unidirectional elastic, torso band adjustably encircling the woman's thoracic torso immediately below the inframammary skinfold and a slightly narrower, adjustable plush pile, unidirectional elastic, breast strap secured at the top center back edge of the torso band for elastically restraining and shaping the woman's new breasts.

1 Claim, 6 Drawing Sheets

BREAST SLING

RELATED APPLICATIONS

This Application relates to U.S. Provisional Patent Application Ser. No. 60/622,387 filed Oct. 27, 2004 entitled BREAST SLING, which is incorporated herein by reference in its entirety, and claims any and all benefits to which it is entitled thereby.

BACKGROUND OF THE INVENTION

1. Field of the Invention

This invention relates generally to a support sling for positioning, stabilizing and supporting human breasts after cosmetic or reconstructive breast surgery.

2. Description of the Prior Art

Cosmetic breast surgeries and surgical breast reconstruction following a mastectomy typically require that the newly configured breasts be stably positioned and supported on the underlying tissues postoperatively. In particular, breast implants tend to move postoperatively in the case of breast augmentation and breast reconstructions (See U.S. Pat. No. 5,037,348, F. G. Farino and U.S. Pat. No. 5,098,331, M. W. Corrado). For mastopexy (breast lift) and mammoplasty (breast reduction) procedures, postoperative support and positioning is critical for reshaping the breast.

In more detail, a woman's breasts consist of a framework of connective tissue and a system of glands and ducts that produce milk. Fat makes up the majority of the breast tissue. Behind the breast tissue are the Pectoralis muscles. The connective tissues supporting the breasts are skin and ligaments, both of which are somewhat elastic and do stretch. Accordingly, distortions due to postoperative swelling caused by excessive buildup of fluid in the tissues responsive to the surgical incisions, and tissue removal must be addressed, in order to assure that the skin and surgically relocated breast tissues properly reattach to underlying supportive tissue layers for the desired breast configuration.

SUMMARY OF THE INVENTION

A breast sling for positioning and stabilizing a woman's breasts following cosmetic or reconstructive breast surgery includes a wide, plush pile, unidirectional elastic, torso band adjustably encircling the woman's thoracic torso immediately below the inframammary skinfold and a slightly narrower, adjustable plush pile, unidirectional elastic, breast strap secured at the top center back edge of the torso band for elastically restraining and shaping the upper and side portions of a woman's breasts, and urging the base of each breast and associated conically rising tissue, downward and inward which, in combination with the encircling elastic torso band, gently stabilzes the position and supports each breast. The wide, plush pile, unidirectional elastic, torso band includes a patch of hook fastener material at one distal end enabling adjustable, overlapping engaging with the plush pile fabric at its other distal end. Similarly, the breast strap has hook fastener material at each of its distal ends enabling various adjustable engagement configurations either with the plush pile, torso band or itself.

The primary advantage of the invented breast sling is its versatility enabling the treating surgeon and associated medical personnel to adjust it to the particular physiognomy of the patient, and to easily readjust it as healing proceeds and swelling decreases and to prevent implant migration

DESCRIPTION OF FIGURES and IMAGES

DESCRIPTION OF PREFERRED AND EXEMPLARY EMBODIMENTS

Figure 1:
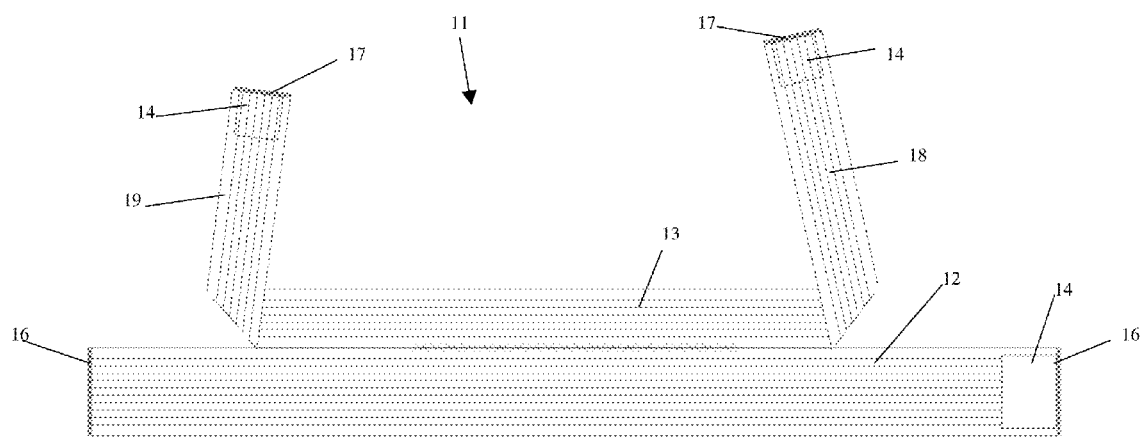
FIG. 1 is a perspective drawing of the invented breast sling.
Figure 2:
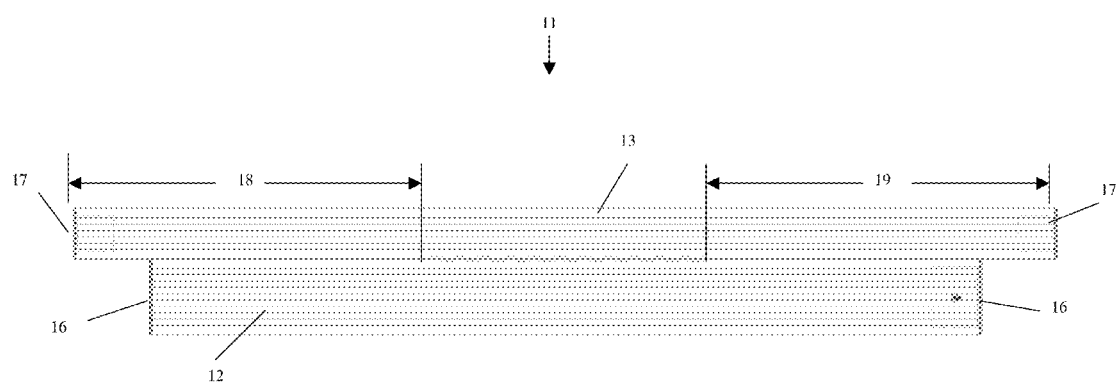
FIG. 2 is a planer top view of the invented breast sling.

Looking at FIGS. 1 & 2 the invented breast sling 11 is formed from a wide, plush pile, unidirectional elastic, torso band 12 and a slightly narrower plush pile, unidirectional elastic, breast strap 13 centrally secured along its bottom edge length to the top edge back of the torso band 12. Velcro hook patches 14 are secured to least one of the distal ends 16 of the torso band 12 and both distal ends 17 of the breast strap 13. The Velcro hook patches 14 each have a width equal to that of the band/strap 12/13 to which it is secured and engage (fasten onto) the plush pile fabric of an underlying band/strap 12/13.

Figure 3:
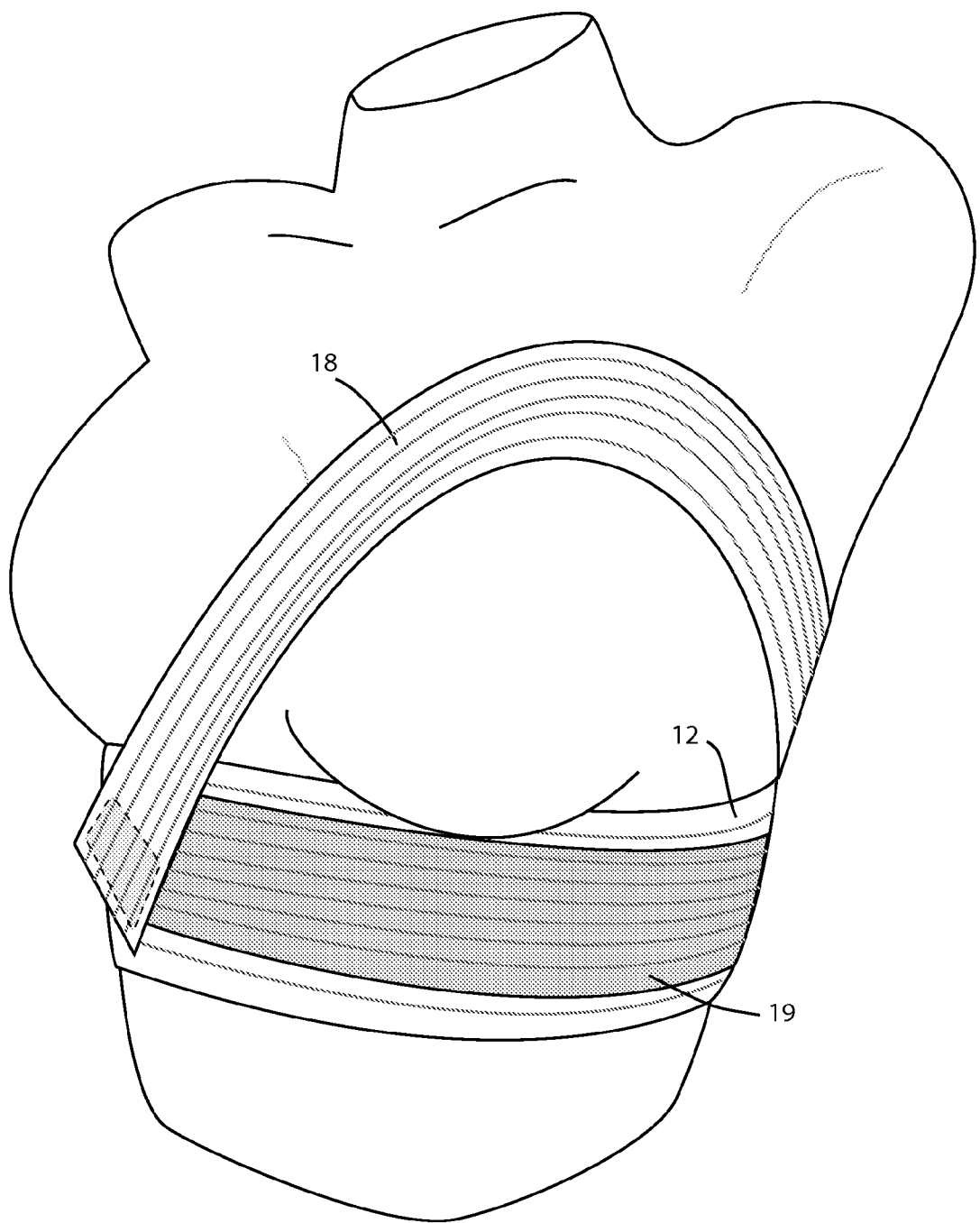
FIG. 3 is a frontal image of a woman's thoracic torso showing the invented breast sling with one length of its plush pile breast strap encircling, positioning and supporting the woman's left breast, the other length of the breast strap encircling and fastened to the encircling plush pile torso band below the woman's right breast.
Figure 4:
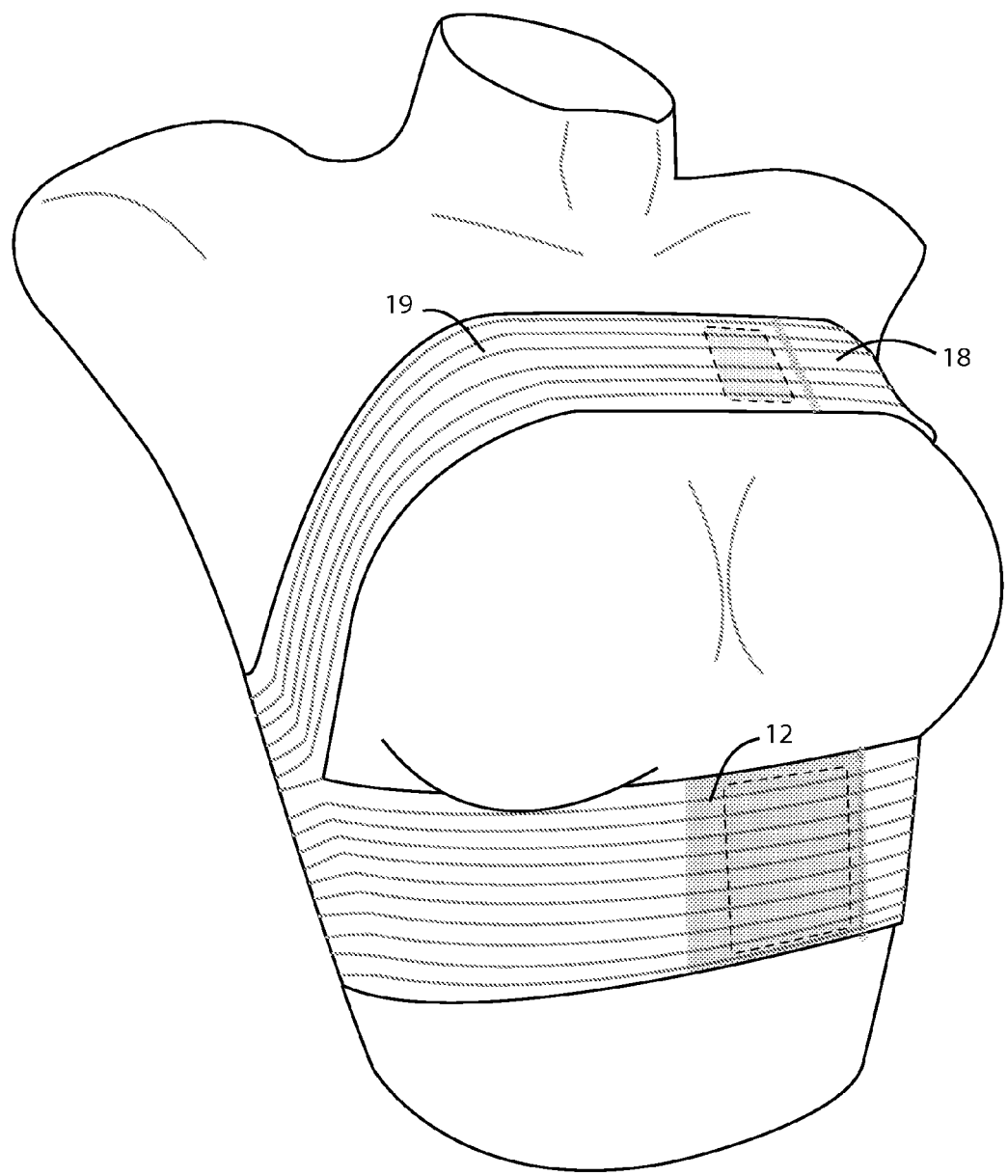
FIG. 4 is again a frontal image of a woman's thoracic torso showing the invented breast sling with the extending ends of the breasts strap secured together in overlapping engagement over the top poles of both of the woman's breasts, with the plush pile torso band encircling the woman's torso just below the inframammary skinfold.
Figure 5:
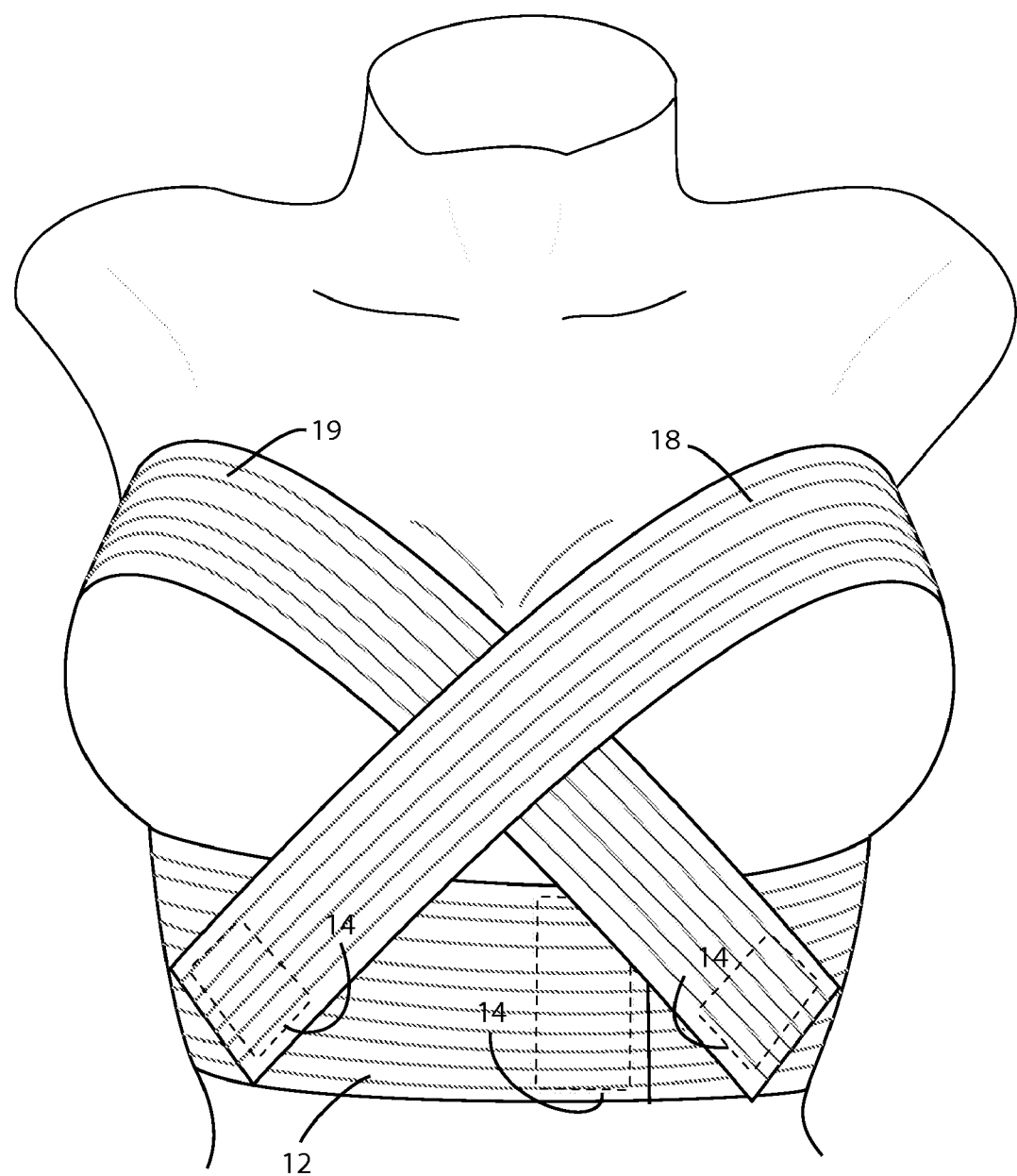
FIG. 5 is another frontal image of a woman's thoracic torso showing the invented breast sling with the extending lengths of the plush pile breast strap crossing over and around the upper poles of the woman's breasts and secured to the plush pile torso band encircling the woman's torso just below the inframammary skinfold.

The torso band 12 is wrapped around a woman's thoracic torso immediately below the inframammary skinfold. (See FIGS. 3-6.) Tension of the torso band 12 is determined by the degree of overlap of the band's distal ends 16. The extending left and right lengths 18 & 19 of the breast strap 13 can be wrapped over and around the respective left and right breasts of the woman (FIG. 5), over the top poles of both breasts (FIG. 4), and over and around one breast and under the other breast (FIG. 3). Tension in the respective lengths 18 & 19 of the breast strap is determined by where the Velcro patches 14 hook onto the plush pile fabric of the underlying band/strap 12 or 13.

The invented breast slings are manufactured in a range of lengths corresponding to the ranges of the torso girths and breast mass (sizes) of women, so that a skilled medical practitioner can choose a size suited to the particular patient. The breast strap 13 is secured centrally along its bottom edge to the top edge of the torso band 12 approximately one third of its unstretched length. In particular, the length of the breast strap 13 fastened to the torso band 12 should approximately be equal that of its extending lengths 18 & 19. The breast strap 13 should also be longer than the torso band 12 because, typically they must be stretched/wrapped around a greater circumference.

Figure 6:
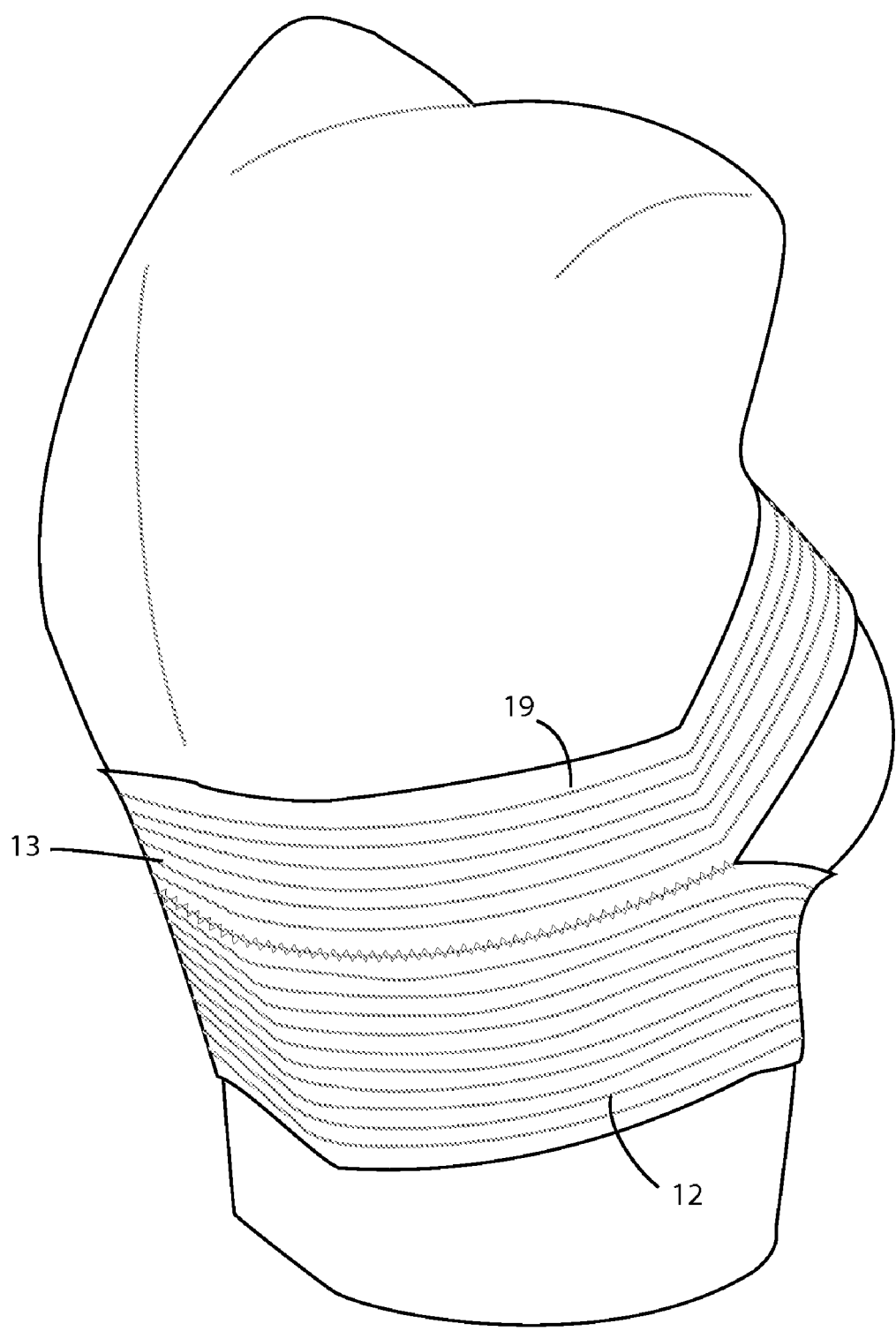
FIG. 6 is right side-rear image of a woman's thoracic torso illustrating the elastic support provided by the encircling plush pile torso band and the right side distal length of the plush pile breast strap of the invented breast sling.

Looking at FIG. 6, it should be appreciated that the ratio of the length of the breast strap 13 fastened to the to upper edge of the torso band 12 can be increased if necessary to provide lateral restraint to the side of the breast to prevent lateral pouching out of the confined breast mass. Such increased lateral fastening may also be accomplished by the medical practioner using tape loops to adjust the angular separation of the extending, diverging, right or left breast strap length 18 and/or 19 upward from the torso band 12. Tape loops can also be utilized to create a supportive web between the angularly diverging breast strap lengths 18 or 19 and the torso band 12.

The unidirectional elastic responses of the torso band 12 and breast strap 13 are longitudinally aligned with the length of the band/strap, not horizontally across the band/strap. Neither the torso band 12 nor the breast strap 13 should be stretched to the upper elastic limit of its plush pile, unidirectional elastic fabric. Nor should the plush pile, unidirectional elastic fabric of the band 12 or strap 13 be under stretched. Stretching of the respective band/strap 12/13 to their respective middle range allows each to elastically respond to increases and decrease in swelling of the underlying healing tissues, as well as to accommodate movements and changes in position of the patient post operatively without significant variations in the tension of the restraining band and strap 12 & 13.

The Velcro® hook patches 14 at the respective distal ends the respective plush pile, unidirectional elastic torso band 12 and strap 13 are secured to the inner surface of the band/strap so that each patch 14 hooks onto the outside surface of the plush pile fabric at the anchoring point on the underlying band or strap. In those instances where the extending left and right extending lengths 18 & 19 of the breast strap 13 are fastened together (FIG. 4), the distal end of the underlying length 18 or 19 should be folded under so that the particular Velcro® patch 14 hooks onto the inner surface of that length and does not poke against the patient's skin. In particular, Velcro® hook material patches are not comfortable when pressed against a patient's skin. Velcro® hook patches can also chafe a patient's skin.

The torso band 12 and breast strap 13 bands of the invented breast sling 11 are preferably, rectangular strips of a unidirectional elastic textile material having plush or pile (plush pile) on both surfaces (interior and exterior) that can engage or fasten to hook fastener material. (See U.S. Pat. No. 2,717, 437, G. de Mestral.). The respective band/strap 12/13 of the invented breast sling each should have a relaxed (unstretched) length slightly less than or equal to the respective circumferential girths of the particular patient's thoracic torso and breasts. The stretched lengths of the band and strap 12 & 13 are determined by the elastic response of the plush pile unidirectional elastic fabric chosen for those components of the breast sling 11. However, as discussed below the unidirectional elastic response of the particular fabric of the band 12 and strap 13 will actually determine a desired relax to stretched length ratios. The basic idea is to provide the medical practioner and patient with the ability to vary the range of tension of the stretched torso band 12 and breast strap 13 by varying the degree of overlap of the of the distal ends in the case of the torso band 12 and the anchor points of the distal ends of the breast strap 13 to the plush pile fabric of the underlying band or strap 12 or 13.

The width of the torso band 11 can range from 2 inches to 6 inches and the breast strap from 2 to four inches. Even wider torso band and breast straps may be appropriate for very large, massive breasted women. The desired goal is for the overlapping, engaged torso band 12 and restraining breast strap 13 to provide a stabilizing distribution of forces coupling and positioning the malleable breast tissues inertially with the woman's thoracic torso. The breast strap 13 should not be so wide that it squashes the breast mass against the underlying muscle tissue and chest wall causing or allowing restraining breast sling to float on the breast mass above the woman's thoracic torso. The torso band 12 should have a sufficient width to assure that the sling does not easily move vertically up or down the woman's torso with properly tensioned.

An example of a suitable unidirectional elastic, textile material for the torso band 12 and breast strap 13 would be a plurality of spaced apart parallel, spandex (elastane) plush pile fiber strips woven/bonded onto an array of transversely oriented, closely spaced, nylon monofilaments to form a band. A producer of such spandex fiber (elastane) is Dupont® Textiles and Interiors.

As described in the art, spandex fiber (elastane) is, . . . "a polymer chain that is a segmented block copolymer containing long, randomly coiled, liquid, soft segments that move to a more linear, lower entropy, structure. The hard segments act as "virtual cross-links" that tie all the polymer chains together into an infinite network. This network prevents the polymer chains from slipping past each other and taking on a permanent set or draw. When the stretching force is removed, the linear, low entropy, soft segments move back to the preferred randomly coiled, higher entropy state, causing the fiber to recover to its original shape and length. Such segmented block copolymer is formed in a multi-step proprietary process. It is extruded into a fiber as a monofilament threadline or for most products into a multiplicity of fine filaments that are coalesced shortly after they are formed into a single threadline."

Essentially, the elastic response of such woven/bonded spandex fiber, plush pile strips is unidirectional in the longitudinal direction of the strips.

Like the spandex, plush pile fiber strips fabric of the torso band 12 and breast strap 13 each elastically stretch longitudinally but not transversely. However, the skilled practitioner, should realize, that the unidirectional longitudinal elastic response of the band and strap only means that the transverse dimension or width of the band does not significantly change (elastically) as the band stretches longitudinally around contours presented by a woman's thoracic torso and associated breasts. However, a consequence is that the tensile force varies transversely across the stretched band as a function of that contour. This means that a skilled medical practioner can orient and position the respective extending lengths 18 & 19 of the breast strap 13, and as well the orientation of the anchor of the overlapping ends of the torso band to achieve a desired distribution of forces for urging, shaping and restraining (locating) one or the other of a woman's breast masses on her thoracic torso. It also means that the medical practioner and patient can adjust the engagement orientation of the respective Velcro® hook material patches 14 at the respective distal ends of the torso band 12 and breast strap to the underlying plush pile strips of the band/strap for a 'sensed' comfort level and effectiveness of restraint for her particular thoracic torso.

I claim:

1. A versatile breast-stabilizing sling for stabilizing, positioning and supporting a woman's breasts after cosmetic or reconstructive surgery, comprising in combination;
    a) a torso band composed of a plush pile, unidirectional elastic fabric at least 2 inches in width, presenting an inside surface, an outside, plush pile surface and a top edge, and having an unstretched length at most equal to a circumferential girth of the woman's thoracic torso immediately below her inframammary skinfold;
    b) a hook material patch adapted to hook into and fasten onto the plush pile outside surface of the torso band secured to the inside surface of the torso band located at a distal end of the torso band, whereby, tension of the torso band wrapping around the woman's thoracic torso below her inframammary skinfold can be adjusted by varying the location where the distal end of the band with the hook material patch overlaps and anchors onto the plush pile, outside surface of the underlying torso band;

c) a breast strap composed of a plush pile, unidirectional elastic fabric lying parallel to, and in a common plane with, and above the torso band, wherein the breast strap has an unstretched length greater than that of the unstretched torso band, and a stretched length sufficient to extend, looping around the woman's thoracic torso, both over and under the woman's breasts, and wherein the top edge of a central back section of the unstretched torso band is attached along a bottom edge of a central back section of the unstretched breast strap from one third to one half the breast strap's length for providing a flat, single layer, central back section of the sling with extending distal torso band lengths and extending distal breast strap lengths, the breast strap also presenting an inside surface and an outside, plush pile surface and having a width slightly narrower than the torso band;

d) hook material patches adapted to hook into and fasten onto the plush pile outside surface of the breast strap secured to the inside surface of the breast strap at its respective distal ends, wherein the extending distal breast strap lengths are variously stretchable, wrapping around to, and across the woman's front thoracic torso and breasts with the hook material patches secured to its inside surface at the respective distal ends anchoring onto the outside, plush pile surfaces of the torso band and the other extending distal breast strap length;

whereby, the breast-stabilizing sling encircles around the woman's thoracic torso with its central back sling section stretching, in a single, flat layer, across the woman's back thoracic torso, the extending distal torso band lengths stretching, extending around, overlapping across the woman's front thoracic torso immediately under the woman's inframammary skinfold, allowing the hook material patch on the inside surface of the distal end of the torso band to variously anchor onto the plush pile, outside surface of the underlying distal torso band length, and the extending distal breast strap lengths stretching, looping around, over and/or under the woman's breasts, with the hook material patches on the inside distal end surfaces of the strap lengths variously fastening onto the outside push pile surfaces of the torso band and/or other breast strap length across the woman's front thoracic torso for inertially stabilizing, positioning and supporting one or both of the woman's breasts.

* * * * *